United States Patent [19]

Makise et al.

[11] Patent Number: 4,754,025
[45] Date of Patent: Jun. 28, 1988

[54] GLUCOSAMINE DERIVATIVES AND REAGENT FOR ASSAYING N-ACETYL-β-D-GLUCOSAMINIDASE USING THE SAME AS SUBSTRATE

[75] Inventors: Junko Makise; Kazuo Ichikawa; Kenji Yoshida; Suzuo Watanabe, all of Kanagawa, Japan

[73] Assignee: Meiji Seika Kaisha, Ltd., Japan

[21] Appl. No.: 795,954

[22] Filed: Nov. 7, 1985

[30] Foreign Application Priority Data

Nov. 7, 1984 [JP] Japan ................. 59-233327

[51] Int. Cl.$^4$ .................... C07H 5/06; C07H 15/22
[52] U.S. Cl. .................. 536/17.7; 536/17.2; 536/17.9; 536/103
[58] Field of Search ............... 435/188, 18; 536/17.2, 536/17.9, 17.7, 103

[56] References Cited

U.S. PATENT DOCUMENTS 4,451,563  5/1984  Kaufman .......................... 435/22

OTHER PUBLICATIONS

Cocker et al (1975), Journal of the Chemical Society, Perkin Trans. 2, vol. 13, pp. 1391–1395.
Ballardie et al (1973), Journal of the Chemical Society, Perkin Trans. 1, vol. 20, pp. 2418–2419.
Chemical Abstracts (1982), vol. 96, p. 338, item #11704r.
Chemical Abstracts (1982), vol. 97, p. 314, item #140846h.
Jones et al (1980), Journal of Biological Chemistry, vol. 255, No. 24, pp. 11861–11869.
Tanaka et al (1976) Chem. Pharm. Bull., vol. 24, No. 12, pp. 3144–3148.
Ballardie et al (1976), Carbohydrate Research, vol. 49, pp. 79–92.
Cocker et al (1976), Journal of the Chemical Society, Perkin II, vol. 5, pp. 618–620.

*Primary Examiner*—Robert J. Warden
*Assistant Examiner*—William J. Herald
*Attorney, Agent, or Firm*—Sughrue, Mion, Zinn, Macpeak, and Seas

[57] ABSTRACT

A glucosamine derivative is disclosed, represented by formula (I)

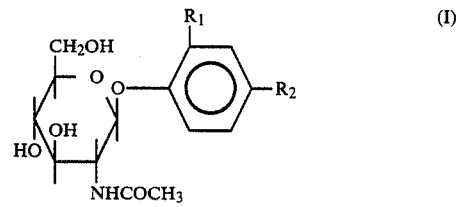

wherein $R_1$ and $R_2$ independently represent a halogen atom or a nitro group. A reagent for assaying N-acetyl-β-D-glucosaminidase containing the glucosamine derivative as a substrate can assay a number of specimens with high sensitivity and accuracy in a short period of time.

3 Claims, 1 Drawing Sheet

GLUCOSAMINE DERIVATIVES AND REAGENT FOR ASSAYING N-ACETYL-β-D-GLUCOSAMINIDASE USING THE SAME AS SUBSTRATE

FIELD OF THE INVENTION

This invention relates to a substrate for assaying N-acetyl-β-D-glucosaminidase (hereinafter referred to as NAGase) that is an indicator for various renal diseases and to a reagent for assaying NAGase using the substrate.

BACKGROUND OF THE INVENTION

Widely employed substrates for assaying NAGase include p-nitrophenyl N-acetyl-β-D-glucosaminide as disclosed in *Biochemical Preparations*, 10: 118 (1963) and 4-methylumbelliferyl N-acetyl-β-D-glucosaminide as disclosed in *Clinica Chimica Acta*, 69(1): 85–91 (1976). The former substrate is disadvantageous in that a blank test is required for each specimen and the procedure for assaying is complicated. The latter substrate requires special appliances, such as a fluorophotometer. Further, m-cresol sulfophthalyl N-acetyl-β-D-glucosaminide is known as an improved substrate for NAGase which does not need a blank test as described in U.S. Pat. No. 4,433,139 corresponding to European Pat. No. 0060793. However, since the assay method using this substrate is an end point method wherein a reagent for stopping an enzymatic reaction is added to the system and a color thus developed under an alkaline condition is determined, the assay should be done in a two-reagent system and also takes time so that apparatuses for automatization are limited.

SUMMARY OF THE INVENTION

As a result of extensive studies conducted to overcome the above-described disadvantages associated with the known substrates, the present inventors have found a novel substrate for assaying NAGase activity and an NAGase-assaying reagent using the same which enables assay of a number of specimens with high sensitivity and accuracy in a short period of time.

That is, the present invention is directed to a novel N-acetyl-β-D-glucosamine derivative represented by formula (I)

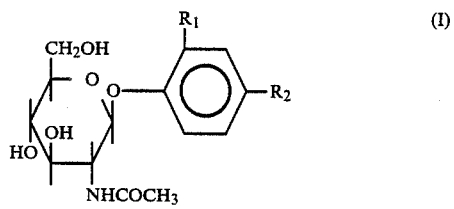

wherein $R_1$ and $R_2$ independently represent a halogen atom or a nitro group.

The present invention is further directed to an NAGase-assaying reagent using the N-acetyl-β-D-glucosamine derivative (I) as a substrate.

Conventional substrates for assaying NAGase cannot be used except in an end point method which involves addition of an alkaline reaction stopping solution to develop a color. To the contrary, the substrate according to the present invention enables determination of NAGase activity in a rate method without using a reaction stopping reagent, in which a difference in absorbance of NAGase between two optionally selected points over a predetermined time interval is measured in the course of the enzymatic reaction. Therefore, the assay method using the substrate of this invention can be applied to commonly employed and commercially available measuring devices and can realize high-accuracy assaying of a number of specimens in a short period of time. In addition, the assay method of this invention may also be applied to an end point system similarly to the conventional assay methods.

DETAILED DESCRIPTION OF THE INVENTION

Figure 1:
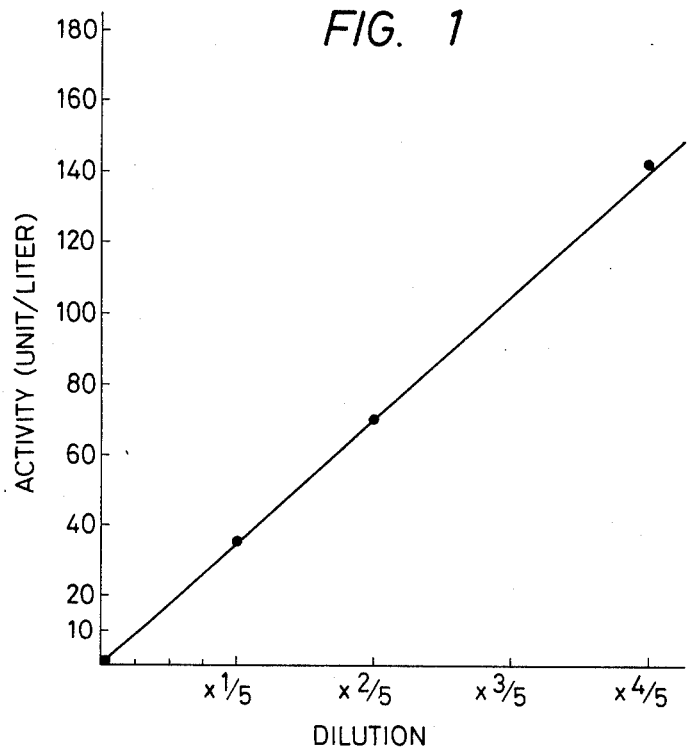
FIG. 1 is a graph showing relation between the activity of N-acetyl-β-D-glucosaminidase using an N-acetyl-β-D-glucosamine derivative of the present invention and dilution.

In the above-described formula (I), the halogen atom represented by $R_1$ or $R_2$ includes a fluorine atom, a chlorine atom, a bromine atom and an iodine atom, with a chlorine atom being preferred. A preferred combination of the substituents $R_1$ and $R_2$ is a chlorine atom for $R_1$ and a nitro group for $R_2$. Specific examples of the compound of formula (I) are 2-chloro-4-nitrophenyl N-acetyl-β-D-glucosaminide and 4-chloro-2-nitrophenyl N-acetyl-β-D-glucosaminide.

The compound of formula (I) can easily be synthesized by condensing 1-chloro-1-deoxy-2,3,4,6-tetraacetyl-α-D-glucosamine represented by formula (II)

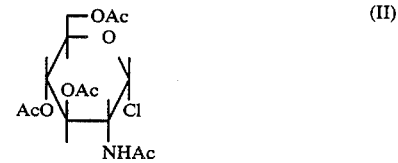

wherein Ac represents an acetyl group, with a phenol derivative represented by formula (III)

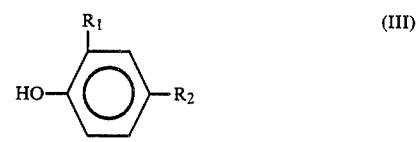

wherein $R_1$ and $R_2$ are as defined above, and releasing a part of the acetyl groups of the resulting product in a usual manner. The compound of formula (II) is known per se, as described in *Biochemical Preparations*, 10: 118 (1963), and the aglycone of formula (III) is easily available as a commercial product.

In carrying out an assay of NAGase activity, the compound (I) is dissolved in a buffer solution (pH 3.5 to 7.0), e.g., a citrate buffer solution, and reacted with a specimen combined with the solution, whereby the substrate (I) is hydrolyzed by the action of NAGase in the specimen to release the aglycone (III), which immediately develops a color. The thus-released aglycone is quantitatively measured by the use of an apparatus for rate assaying such as Hitachi 705, Hitachi 736 and COBAS-BIO. Further, the reaction may be stopped after the elapse of a predetermined time by addition of an alkali solution or an inhibitor such as $Hg^{++}$ and $Ag^{++}$, and the system is then subjected to colorimetric analysis.

Procedures for the above-described assay methods will hereinafter be described in more detail.

A. Rate Assay Method:

A predetermined amount, e.g., from 2.5 to 100 μl, of a specimen, e.g., urine or serum, is added to a predetermined amount, e.g., from 2 to 5 mM, in from 50 μl to 1.25 ml of a substrate solution, followed by allowing the system to react at 37° C. for a predetermined period of time, e.g., from 4.5 to 15 minutes. A difference in absorbance at around 400 nm between two optionally selected points is measured by means of a spectrophotometer.

B. Manual Method:

A 1.0 ml portion of a substrate solution (2 to 5 mM) is placed in a 10 ml-volume test tube, and 1.0 ml of a blank solution (pH 3.5 to 7.0) is placed in a 10 ml-volume test tube. After heating both test tubes at 37° C. for 5 minutes, 100 μl of a specimen (urine or serum) is added to the test tube containing the substrate, followed by allowing the system to react at 37° C. for 15 minutes. After 15 minutes of the reaction, a reaction stopping reagent is added to the reaction system to stop the reaction. To the blank solution in another test tube is added 100 μl of distilled water, followed by reacting under the same conditions as above. After the reaction, a reaction stopping reagent is added thereto to stop the reaction. The absorbance of the specimen and that of the blank solution are determined at 400 nm, which is the maximum absorption wavelength of the released aglycone, using, as a control, the substrate blank and water, respectively.

Since the substrate according to the present invention, e.g., 2-chloro-4-nitrophenyl N-acetyl-β-D-glucosaminide (hereinafter referred to as 2CNP-NAG), is sparingly soluble in a buffer solution suitable for assaying NAGase, sufficient sensitivity sometimes cannot be obtained with such a low concentration of substrate solution (2CNP-NAG) by using commercially available and generally employed apparatuses for measurement. Such being the case, the substrate may be dissolved in a combination of a non-aqueous solvent and an inclusion compound. This method brings about not only improved solubility of the substrate but also increased sensitivity in assaying.

The inclusion compound which can be used includes crown ethers, e.g., 18-crown-6, 15-crown-5, 12-crown-4, etc,; and cyclodextrin or derivatives thereof, e.g., α-cyclodextrin, β-cyclodextrin, γ-cyclodextrin, dimethyl α-cyclodextrin, dimethyl β-cyclodextrin, dimethyl γ-cyclodextrin, L-poly-β-cyclodextrin, etc. These inclusion compounds may be used individually or in combinations of two or more thereof. Among the above-recited inclusion compounds, crown ethers are particularly preferred. The inclusion compounds are usually used in amounts of not less than 3 molecules, and preferably from 30 to 150 molecules, per molecule of 2CNP-NAG. Examples of the non-aqueous solvent which can be used for dissolving the substrate are glycols, e.g., ethylene glycol, diethylene glycol, propylene glycol, etc., and aliphatic alcohols, e.g., ethanol, methanol, etc., with glycols being particularly preferred. These solvents may be used individually or as a combination thereof.

As mentioned before, in the conventional assay methods using p-nitrophenyl N-acetyl-β-D-glucosaminide or m-cresol sulfophthalyl N-acetyl-β-D-glucosaminide as substrates, after the system is allowed to react for 15 to 30 minutes, a reaction stopping solution is added to the system to stop the reaction, and the reaction mixture having developed a color, is determined for absorbance.

To the contrary, according to the rate assay method of this invention, the enzymatic reaction immediately develops a color. Therefore, the assay can be carried out in a short period of time through a simple operation by measuring a difference in absorbance between two optionally selected points in the course of the reaction. In other words, as compared with the conventional substrates modified with 4-nitrophenol, when the substrate of this invention is used, a pKa value of the released 2-chloro-4-nitrophenol is noted at around 5.5. Accordingly, NAGase can be assayed with high sensitivity in the present invention.

The present invention will now be illustrated in greater detail with reference to the following examples, but it should be noted that these examples are to be understood as not limiting the present invention.

TEST EXAMPLE 1

In an apparatus for rate assaying, Hitachi 705, were placed 20 μl of a specimen and 400 μl of a buffer solution (pH 5.0, 0.1M citrate buffer), and then 100 μl of a substrate solution containing 1.5 mM of a substrate, 6 wt% of 15-crown-5 and 6 wt% of ethylene glycol, and reaction at 37° C. and evaluation of NAGase were performed automatically. The results show good liniarity of NAG activity v. dilution as shown in FIG. 1.

TEST EXAMPLE 2

Figure 2:
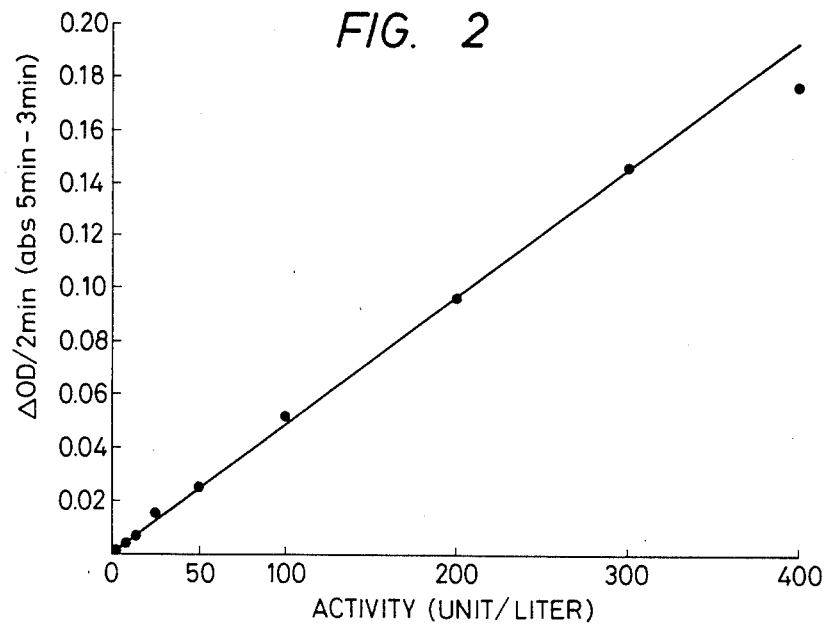
FIG. 2 is a graph representing a standard curve for manual assay of N-acetyl-β-D-glucosaminidase using an N-acetyl-β-D-glucosamine derivative of the present invention as a substrate.

A 0.5 ml portion of a substrate solution was placed in a 10 ml-volume test tube, and 0.5 ml of a blank solution (pH 5.0, 0.1M citrate buffer) was placed in another 10 ml-volume test tube. After heating both test tubes at 37° C. for 5 minutes, 100 μl of a specimen (urine) was added to the test tube containing the substrate followed by allowing the system to react at 37° C. After 3 minutes of the reaction, a reaction stopping reagent was added to the reaction system to stop the reaction. On the other hand, 100 μl of distilled water was added to another test tube containing the blank solution only followed by reacting under the same conditions as above. After 3 minutes of the reaction, a reaction stopping reagent was added thereto to stop the reaction. The absorbance of the specimen and that of the blank solution were determined at 400 nm. The above procedures were repeated except for the reaction was continued for 5 minutes and the absorbance of the specimen and that of the blank solution were determined in the same manner as above. Then, the increase in the absorbance, i.e., ΔOD/2 min. (abs. 5 min–3 min) was obtained. In this manner, a standard curve for assaying NAGase using the N-acetyl-β-D-glucosamine derivative (I) of the present invention as a substrate as shown in FIG. 2 was obtained.

EXAMPLE 1

2-Chloro-4-Nitrophenyl N-Acetyl-β-D-Glucosaminide (1) In 80 ml of acetone were dissolved 3.65 g (10 mmol) of acetochloroglucosamine [*Biochemical Preparation*, 10: 118 (1963)] and 3.47 g (20 mmol) of 2-chloro- 4-nitrophenol, and 20 ml of a 1N sodium hydroxide aqueous solution was added thereto. The mixture was stirred at room temperature for 5 hours, followed by standing at 4° C. overnight. The reaction mixture was concentrated under reduced pressure, and the residue was washed with water. Recrystallization of the residue from methanol gave 2.1 g of 2-chloro-4-nitrophenyl 2,3,4,6-tetraacetyl-β-D-glucosaminide as white needle crystals having a melting point of 196° C.

IR (KBr): 1760, 1673, 750 cm$^{-1}$

NMR: δ(CDCl$_3$): 1.96 (s, 3H), 2.06 (s, 3H), 2.08 (s, 6H), 3.9–4.5 (4H), 5.18 (t, J=9.0 Hz, 1H), 5.50 (d, J=9.0 Hz, 1H), 5.52 (t, J=9.0 Hz, 1H), 5.85 (d, J=9.0 Hz, 1H), 7.24 (d, J=9.2 Hz, 1H), 8.06 (dd, J=3.5, 9.2 Hz, 1H), 8.26 (d, J=3.5 Hz, 1H)

(2) To 50 ml of dried methanol was added 2.1 g (3.9 mmol) of the product obtained in (1) above, and 0.4 ml of 28% sodium methoxide was added dropwise thereto at room temperature, followed by standing overnight. The crystals formed were separated by filtration, washed with methanol and recrystallized from water to obtain 1.0 g of 2-chloro-4-nitrophenyl N-acetyl-β-D-glucosaminide as white needle crystals having a melting point of 168° C.

IR (KBr): 3280, 1650, 1530, 754 cm$^{-1}$

EXAMPLE 2

4-Chloro-2-Nitrophenyl N-acetyl-β-D-Glucosaminide (1) In the same manner as described in Example 1-(1), except using 20 mmol of 4-chloro-2-nitrophenol in place of 2-chloro-4-nitrophenol, 2.6 g of 4-chloro-2-nitrophenyl 2,3,4,6-tetraacetyl-β-D-glucosaminide was obtained, as white needle crystals having a melting point of 173° C.

IR (KBr): 1740, 1658, 730 cm$^{-1}$

NMR: δ(CDCl$_3$): 1.98 (s, 3H), 2.07 (s, 3H), 2.08 (s, 3H), 2.10 (s, 3H), 3.7–4.4 (4H), 5.10 (t, J=9.0 Hz, 1H), 5.43 (d, J=9.0 Hz, 1H), 5.56 (t, J=9.0 Hz, 1H), 5.94 (d, J=9.0 Hz, 1H), 7.30 (d, J=9.2 Hz, 1H), 7.46 (dd, J=3.5, 9.2 Hz, 1H), 7.76 (d, J=3.5 Hz, 1H).

(2) In the same manner as in Example 1-(2), except using 2.0 g (3.9 mmol) of the product obtained in (1) above, 1.1 g of 4-chloro-2-nitrophenyl N-acetyl-β-D-glucosaminide having a melting point of 179° C. was obtained.

IR (KBr): 3325, 1650, 1540, 728 cm$^{-1}$.

EXAMPLE 3

Assay of NAGase Activity (1) Preparation of Reagent:
Reagent I:

Five milligrams of 2CNP-NAG was added to a mixed solution comprising 500 μl of 15-crown-5 and 500 μl of ethylene glycol (Solution I) and thoroughly dissolved to form a clear solution. The resulting solution was mixed well with 1 ml of a 85% sodium chloride aqueous solution (Solution II) to prepare 2 ml of a substrate solution.

Reagent II:

In about 48 ml of distilled water were dissolved 0.861 g of citric acid (C$_6$H$_8$O$_7$.H$_2$O) and 1.74 g of sodium citrate (C$_6$H$_5$O$_7$Na$_3$.2H$_2$O). After adjusting to a pH of 5.0 (25° C.) with a sodium citrate aqueous solution, distilled water was added to the solution to make 50 ml.

(2) Assay Procedure:

To 1.5 ml of Reagent II was added 0.1 ml of a specimen (urine), and the system was warmed at 37° C. for 3 minutes. Then, 0.5 ml of Reagent I which had previously been warmed at 37° C. was added thereto, followed by stirring. The system was evaluated for increases in absorbance at 405 nm per unit time by the use of a spectrophotometer. As a control, an enzymatic solution having a known activity was assayed in the same manner. The NAGase activity of the specimen was obtained from the ratio of the increase in absorbance of the specimen per unit time to that of the control.

The same procedures as described above were repeated except for using 12-crown-4 or 18-crown-6 in place of 15-crown-2 and using propylene glycol in place of ethylene glycol. In the case of using the solid 18-crown-6, it had been dissolved in ethylene glycol in advance.

As a result, it was confirmed that the specimen contains 20 U/l of NAGase, which level is higher than 15 U/l that shows that the subject is suspected of suffering nephropathy such as nephritis.

EXAMPLE 4

Assay of NAGase Activity (1) Preparation of Reagent:
Reagent I:

Ten milligrams of 2CNP-NAG was added to 3 ml of ethylene glycol (Solution I) and thoroughly dissolved to form a clear solution. The resulting solution was mixed well with 5 ml of a 85% sodium chloride aqueous solution (Solution II) to prepare 8 ml of a substrate solution.

Reagent II:

In about 48 ml of distilled water were dissolved 0.861 g of citric acid (C$_6$H$_8$O$_7$.H$_2$O), 1.74 g of sodium citrate (C$_6$H$_5$O$_7$Na$_3$.2H$_2$O) and 0.4 g of α-cyclodextrin. After adjusting to a pH of 5.0 (25° C.) with a 0.2M citric acid aqueous solution or a sodium citrate aqueous solution, distilled water was added to the solution to make 50 ml.

(2) Assay Procedure:

To 1.0 ml of Reagent II was added 0.1 ml of a specimen, and the system was warmed at 37° C. for about 1 to 5 minutes. One milliliter of Reagent I which had previously been warmed at 37° C. was added thereto, followed by stirring. The system was evaluated for increases in absorbance at 405 nm per unit time by the use of a spectrophotometer. The NAGase activity was determined in the same manner as described in Example 3.

The same procedures as described above were repeated except for using β-cyclodextrin or γ-cyclodextrin in place of α-cyclodextrin and using propylene glycol in place of ethylene glycol.

As a result, it was confirmed that the specimen contains 80 U/l of NAGase.

EXAMPLE 5

Assay of NAGase Activity (1) Preparation of Reagent:
Reagent I:

In a mixture comprising 0.4 ml of 12-crown-4, 0.6 ml of methanol, and 1 ml of water was dissolved 7.8 g of 2CNP-NAG to make a clear solution.

Reagent II:

In about 48 ml of distilled water were dissolved 0.861 g of citric acid (C$_6$H$_8$O$_7$.H$_2$O) and 1.74 g of sodium citrate (C$_6$H$_5$O$_7$Na$_3$.2H$_2$O). After the solution was adjusted to a pH of 5.0 (25° C.) with a 0.2M citric acid aqueous solution or a sodium citrate aqueous solution, distilled water was added thereto to make 50 ml.

Two milliliters of Reagent I and 3 ml of Reagent II were mixed to make 5 ml of a mixed reagent.

(2) Assay Procedure:

To 2 ml of the above prepared mixed reagent which had previously been warmed at 37° C. was added 0.1 ml of a specimen, followed by stirring. The system was evaluated for increases in absorbance at 405 nm per unit time by the use of a spectrophotometer. The NAGase activity was obtained in the same manner as described in Example 3.

The same procedures as described above were repeated, except for using 18-crown-6 or 15-crown-5 in place of 12-crown-4 and using ethanol in place of methanol.

As a result, it was confirmed that the specimen contains 90 U/l of NAGase.

While the invention has been described in detail and with reference to specific embodiments thereof, it will be apparent to one skilled in the art that various changes and modifications can be made therein without departing from the spirit and scope thereof.

What is claimed is:

1. An N-acetyl-β-D-glucosamine derivative represented by formula (I)

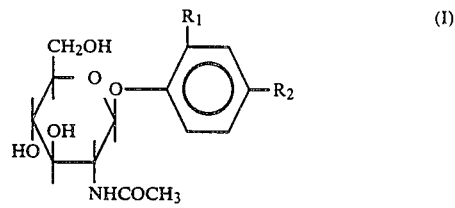

wherein one of $R_1$ and $R_2$ represent a halogen atom and the other of $R_1$ and $R_2$ represents a nitro group.

2. 2-Chloro-4-nitrophenyl N-acetyl-β-D-glucosaminide.

3. 4-Chloro-2-nitrophenyl N-acetyl-β-D-glucosaminide.

* * * * *